US008552060B2

(12) United States Patent
Palumbo et al.

(10) Patent No.: US 8,552,060 B2
(45) Date of Patent: Oct. 8, 2013

(54) METHODS FOR TREATMENT OF SEXUAL DYSFUNCTION

(75) Inventors: Joseph Palumbo, St. Davids, PA (US); Jonathan Sporn, Princeton, NJ (US); Thomas Steckler, Mol/milligem (BE); Yong Choi, Pine Brook, NJ (US); James S. Lee, Montville, NJ (US)

(73) Assignee: SK Biopharmaceuticals Co., Ltd., Seoul (KR)

( * ) Notice: Subject to any disclaimer, the term of this patent is extended or adjusted under 35 U.S.C. 154(b) by 914 days.

(21) Appl. No.: 11/922,128

(22) PCT Filed: Jun. 13, 2006
(Under 37 CFR 1.47)

(86) PCT No.: PCT/US2006/023068
§ 371 (c)(1),
(2), (4) Date: Mar. 26, 2009

(87) PCT Pub. No.: WO2007/001841
PCT Pub. Date: Jan. 4, 2007

(65) Prior Publication Data
US 2009/0221553 A1 Sep. 3, 2009

Related U.S. Application Data
(60) Provisional application No. 60/692,809, filed on Jun. 22, 2005.

(51) Int. Cl.
A61K 31/24 (2006.01)
(52) U.S. Cl.
USPC .......................................... 514/534; 514/540
(58) Field of Classification Search
USPC .................................... 514/534, 540
See application file for complete search history.

(56) References Cited

U.S. PATENT DOCUMENTS

| | | | |
|---|---|---|---|
| 5,955,499 A | 9/1999 | Choi et al. | |
| 6,228,864 B1 * | 5/2001 | Smith et al. | 514/288 |

(Continued)

FOREIGN PATENT DOCUMENTS

| | | |
|---|---|---|
| EP | 0633023 | 1/1995 |
| JP | 9-503231 | 3/1997 |

(Continued)

OTHER PUBLICATIONS

International Search Report and Written Opinion dated Oct. 20, 2006.
NovaScreen: dated: Oct. 24, 1994.

*Primary Examiner* — San-Ming Hui

(57) ABSTRACT

This invention is directed to a method of treating sexual dysfunction in a subject, comprising the step of administering a therapeutically effective amount of a compound of Formula (I): or a pharmaceutically acceptable salt or ester thereof wherein Rx is a member selected from the group consisting of hydrogen, lower alkyl of 1 to 8 carbon atoms, halogen selected from F, CI, Br and I, alkoxy containing 1 to 3 carbon atoms, nitro, hydroxy, trifluoromethyl, and thioalkoxy containing 1 to 3 carbon atoms; x is an integer of 1 to 3, with the proviso that R may be the same or different when x is 2 or 3; $R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and O to 1 oxygen atom, wherein the nitrogen atoms are not directly connected with each other or with the oxygen atom.

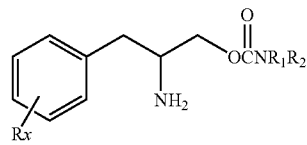

32 Claims, 1 Drawing Sheet

(56) References Cited

U.S. PATENT DOCUMENTS

2005/0203130 A1 9/2005 Buntinx
2009/0312416 A1 12/2009 Ahnaou et al.

FOREIGN PATENT DOCUMENTS

| WO | WO 96/24577 | 8/1996 |
| WO | WO 2006/050037 | 5/2006 |

* cited by examiner

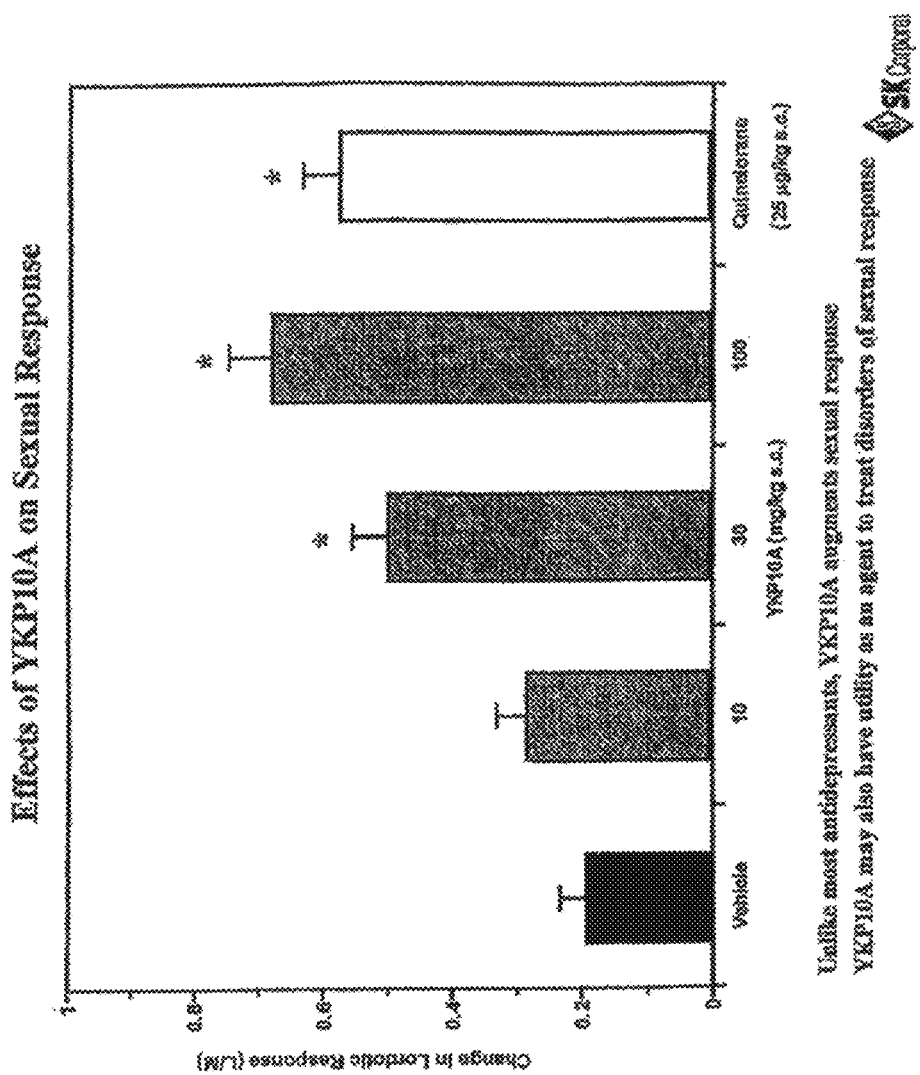

METHODS FOR TREATMENT OF SEXUAL DYSFUNCTION

CROSS-REFERENCE TO RELATED APPLICATIONS

This application is a national phase application of PCT Application No. PCT/US2006/023068, filed on Jun. 13, 2006, which claims the benefit and priority of U.S. Patent Application No. 60/692,809, filed Jun. 22, 2005. The entire disclosures of the applications identified in this paragraph are incorporated herein by references.

BACKGROUND OF THE INVENTION

1. Field of Invention

The present invention relates generally to the fields of pharmacology, urology and psychiatry and to methods of treating sexual dysfunction. More specifically, this invention provides methods for the use of certain carbamate compounds for use alone or in combination with other medications for the treatment of sexual dysfunction in human females or males 2. Description of Related Art Masters and Johnson defined sexual dysfunction as "the persistent impairment of normal or usual patterns of sexual interest and/or response" (Masters et al., Human Sexual Response, Boston, Mass.: Little, Brown and Co. 1966). The problem came to national attention when the results of the National Health and Societal Life Survey were published in 1999. Interviews with over 3000 American men and women aged 18-59 revealed that 31% of men and 43% of women (about 40 million) experienced some degree of sexual dysfunction. The scope of the problem was such that it was said to "warrant recognition as a significant public health concern." See Laumann et al., "Sexual Dysfunction in the United States: prevalence and predictors," JAMA 281:537 (1999). Although sexual dysfunction rarely threatens physical health, it can take a heavy psychological toll, bringing on depression, anxiety, and debilitating feelings of inadequacy.

Sexual dysfunction (SD) is a significant clinical problem that can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes self-esteem and disrupts personal relationships thereby inducing personal distress. In the clinic, SD disorders have been divided into female sexual dysfunction (FSD) disorders and male sexual dysfunction (MSD) disorders (Melman et al 1999 J. Urology 161, 5-11). FSD is best defined as the difficulty or inability of a woman to find satisfaction in sexual expression.

Male sexual dysfunction (MSD) is generally associated with either erectile dysfunction, also known as male erectile dysfunction (MED) and/or ejaculatory disorders such as premature ejaculation or rapid ejaculation (PED), anorgasmia (unable to achieve orgasm) or male orgasmic disorder (MOD) or desire disorders such as hypoactive sexual desire disorder (lack of interest in sex) (HSDD) and can result from a variety of causes, including physical illness, depression, hormonal abnormality or medications that affect libido or performance.

Recent studies suggest that, at least, 43% of woman have some form of sexual dysfunction (See above, Lauman et al. JAMA, 281:537, 1999). These can be categorized into four main areas: 1) sexual desire disorders, namely hypoactive sexual desire or sexual aversion disorder; 2) sexual arousal disorders; 3) orgasmic disorders; and 4) sexual pain disorders which include dyspaureunia and vaginismus.

The dominant category of female sexual dysfunction (FSD) is female sexual arousal disorder (FSAD), which affects up to 75% of women diagnosed with FSD.

The categories of female sexual dysfunction (FSD) are best defined by contrasting them to the phases of normal female sexual response: desire, arousal and orgasm (see S R Leiblum, (1998), Definition and Classification of Female Sexual Disorders, Int. J. Impotence Res., 10, S104-S106). Sexual desire or libido is the drive for sexual expression. Its manifestations include sexual thoughts and fantasies. Arousal includes the vascular response to sexual stimulation, an important component of which is genital engorgement and increased vaginal lubrication, elongation of the vagina and increased genital sensation/sensitivity and a subjective excitement response. Orgasm is the release of sexual tension that has culminated during arousal. Hence, Female Sexual Disorder (FSD) occurs when a woman has an absent, inadequate or unsatisfactory response in any one or more of these phases, usually desire, arousal or orgasm.

The American Psychiatric Association classifies female sexual dysfunction (FSD) into four classes: FSAD, hypoactive sexual desire disorder (HSDD), female orgasmic disorder (FOD), and sexual pain disorders (e.g. dyspareunia and vaginismus) [see the American Psychiatric Association's Diagnostic and Statistical Manual of Mental Disorders, 4th Edition (DSM-IV)]. DSM-IV defines the four classes as follows:

HSDD—Persistently or recurrently deficient (or absent) sexual fantasies and desire for sexual activity that causes marked distress or interpersonal difficulties. The judgement of deficiency or absence is made by the clinician, taking into account factors that affect functioning, such as age and the context of the person's life.

FSAD—Persistent or recurrent inability to attain, or to maintain until completion of the sexual activity, an adequate lubrication-swelling response of sexual excitement FOD—Persistent or recurrent delay in, or absence of, orgasm following a normal sexual excitement phase. Women exhibit wide variability in the type or intensity of stimulation that triggers orgasm. The diagnosis of FOD should be based on the clinician's judgement that the woman's orgasmic capacity is less than would be reasonable for her age, sexual experience, and the adequacy of the sexual stimulation she receives.

Sexual Pain Disorders such as Dyspareunia and Vaginismus. Dyspareunia is the recurrent or persistent genital pain associated with sexual intercourse. Vaginismus is the recurrent or persistent involuntary spasm of the musculature of the outer third of the vagina that interferes with sexual intercourse.

The American Foundation for Urologic Disease has also developed definitions using the same four classes (see The Journal of Urology, 2000, Vol 163, page 888-893). The definitions are very similar to those of the DSM-IV:

1) HSDD is the persistent or recurrent deficiency (or absence) of sexual fantasies/thoughts, and/or desire for or receptivity to sexual activity, which causes personal distress.

HSDD is present if a woman has no or little desire to be sexual, and has no or few sexual thoughts or fantasies. This type of FSD can be caused by low testosterone levels, due either to natural menopause or to surgical menopause. Other causes in both pre-menopausal woman (i.e. woman who are pre-menopausal and who have not have hysterectomies) as well as post menopausal women include illness, medications, fatigue, depression and/or anxiety. Factors having a potential (conscious or sub-conscious) psychological impact such as relationship difficulties or religious factors may be related to the presence of/development of HSDD in females.

The term significant HSDD means a level of HSDD which causes some degree of personal distress to the female subject. Preferably significant HSDD means a level of HSDD which causes some degree of distress and is measurable, for example, through evaluation by a clinician using a semi-structured questionnaire.

2) FSAD is the persistent or recurrent inability to attain or maintain sufficient sexual excitement, causing personal distress, which may be expressed as a lack of subjective excitement, or genital (lubrication/swelling) or other somatic responses.

FSAD is a highly prevalent sexual disorder affecting pre-, peri-, and post menopausal women. It is associated with concomitant disorders such as depression, cardiovascular diseases, diabetes and UG disorders. FSAD is characterized by inadequate genital response to sexual stimulation. The genitalia do not undergo the engorgement that characterizes normal sexual arousal. The vaginal walls are poorly lubricated, so that intercourse is painful. Orgasms may be impeded. FSAD can be caused by reduced estrogen at menopause or after childbirth and during lactation, as well as by illnesses, with vascular components such as diabetes and arteriosclerosis. Other causes result from treatment with diuretics, antihistamines, antidepressants e.g. selective serotonin reuptake inhibitors or antihypertensive agents.

3) FOD is the persistent or recurrent difficulty, delay in or absence of attaining orgasm following sufficient sexual stimulation and arousal, which causes personal distress.

4) Sexual pain disorders: Dyspareunia is the recurrent or persistent genital pain associated with sexual intercourse. Vaginismus is the recurrent or persistent involuntary spasm of the musculature of the outer third of the vagina that interferes with vaginal penetration, which causes personal distress. Dyspareunia and vaginismus are characterised by pain resulting from penetration and sexual activity and may be caused by medications which reduce lubrication, endometriosis, pelvic inflammatory disease, inflammatory bowel disease or urinary tract problems.

The etiology of sexual dysfunction, in both men and women, may include vascular/endothelial disease such as hypertension, neurological disorders, and hormonal disorders, such as decreased levels of estrogen and/or testosterone. Sexual dysfunction in both men and women can also be caused, or exacerbated, by medication such as antidepressants, antihypertensive and many other classes of commonly used medication. Given the extensive use of these medication by all ages and both sexes it is especially important to develop means of treating medication induced sexual dysfunction.

Clearly FSD especially, is a complex disorder with more active clinical issues than the corresponding male disorder, penile erectile dysfunction (MED). Hence it is not surprising that to date there has been little success in treating FSD, and use of treatments that are successful in treating MED, such as sildenafil, have shown only limited success in ameliorating FSD. It may be that a different spectrum of activities, mechanisms, dosing regimens and duration of action of agents is needed when devising treatments for women, relative to approaches taken with men. But treatments for sexual dysfunction of all types in both men and women, with the partial exception of MED, is inadequate and thus there is a great clinical need for such treatments.

SUMMARY OF THE INVENTION

The present invention is directed to methods of treating sexual dysfunction in a subject, comprising the step of the administration, to a subject in need of such treatment, of a therapeutically effective amount a compound of the Formula (1):

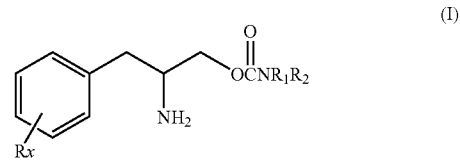

or a pharmaceutically acceptable salt or ester thereof; wherein

Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom.

Embodiments of the invention include methods of treating sexual dysfunction in a subject, comprising the step of the administration, to a subject in need of such treatment, of a therapeutically effective amount of an enantiomer of Formula 1 substantially free of other enantiomers or an enantiomeric mixture wherein one enantiomer of Formula 1 predominates;

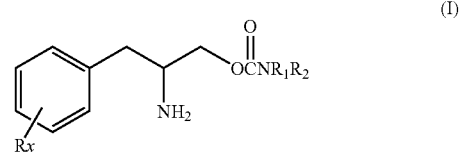

or a pharmaceutically acceptable salt or ester thereof; wherein

Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom.

Preferably, wherein Rx, R1 and R2 are all selected from hydrogen.

Preferably wherein one enantiomer selected from the group consisting of Formula 1 predominates to the extent of about 90% or greater.

More preferably, wherein one enantiomer selected from the group consisting of Formula 1 predominates to the extent of about 98% or greater.

Embodiments of the invention include a method for using the enantiomer selected from the group consisting of Formula 1 for the preparation of a medicament for the treatment of sexual dysfunction,

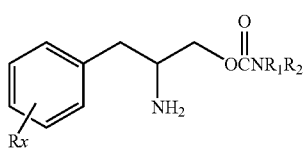
(I)

or a pharmaceutically acceptable salt or ester thereof
wherein

Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom.

Embodiments of the invention include a method for using the enantiomer of Formula 1 substantially free of the other enantiomers that is the enantiomer of Formula 1b or an enantiomeric mixture therein the enantiomer of Formula 1b predominates. This is the dextrorotary (D) enantiomer that is of absolute configuration (R).

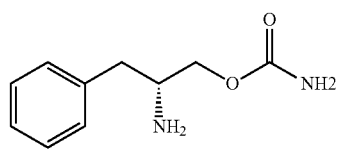
Formula 1b wherein the enantiomer of Formula 1b predominates to the extent of about 90% or greater.

More preferably, wherein an enantiomer of Formula 1b predominates to the extent of about 98% or greater.

Embodiments of the invention also include methods wherein the carbamate compounds of the invention are administered concomitantly with other medications that may themselves cause sexual dysfunction in order to prevent, reverse or minimizes this unwanted side effect.

Such other medications include but are not limited to; conventional antidepressants and other psychiatric medications that include but are not limited to; selective serotonin reuptake inhibitors (SSRI's); selective serotonin and norepinephrine reuptake inhibitors (SNRI's); older tricyclic antidepressants (TCAs); monoamine oxidase inhibitors (MAO-inhibitors), reversible inhibitors of monoamine oxidase (RIMAs), tertiary amine tricyclics and secondary amine tricyclic antidepressants, antipsychotics, anticonvulsants, lithium carbonate, and including but not limited to fluoxetine, duloxetine, venlafaxine, milnacipran, citalopram, fluvoxamine, paroxetine, sertraline, 5-MCA-NAT, lithium carbonate ($liCO_3$), isocarboxazid, phenelzine, tranylcypromine, selegiline, moclobemide, amitriptyline, clomipramine, doxepin, imipramine, trimipramine, amoxapine, desipramine, maprotiline, nortriptyline and protriptyline, kappa opioid receptor antagonists; selective neurokinin antagonists, corticotropin releasing factor (CRF) antagonists, antagonists of tachykinins, α-adrenoreceptor antagonists, and other types of medications such as; antihypertensive medications, cardiac medications such as calcium channel blockers, ACE inhibitors, statins, etc and pharmaceutically acceptable salts thereof and wherein the therapeutically effective amount of enantiomer is from about 0.01 mg/kg/dose to about 300 mg/kg/dose.

BRIEF DESCRIPTION OF THE FIGURES

FIG. 1 shows the effect of increasing doses of test compound on the lordotic response in female rats as compared to vehicle and the active control quinelorane.

DETAILED DESCRIPTION OF THE INVENTION

The present invention is directed to a method of treatment of sexual dysfunction. The method comprising, administering to a subject in need thereof a therapeutically effective amount of a compound selected from the group consisting of phenylalkylamino carbamates.

The invention features compounds of Formula 1:

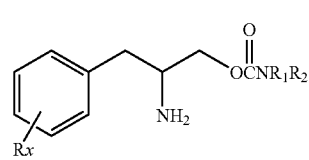
Formula 1 or enantiomers, diastereomers, racemates or mixtures thereof, or hydrates, solvates and pharmaceutically acceptable salts, esters and amides thereof: wherein;

Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the cyclic compound can comprise 0 to 2 nitrogen atoms and 0 to 1 oxygen atoms, wherein the nitrogen atoms are not directly connected with each other or with the oxygen atom and the pharmaceutically acceptable salts and esters thereof.

The present method also includes the use of a compound selected from the group consisting Formula 1 wherein Rx, R1 and R2 are preferably selected from hydrogen, this is Formula 1a below;

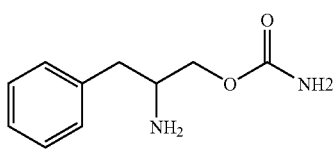

Formula 1a

The present method also preferably includes the use of the D (or dextrorotary) enantiomer (of absolute configuration R) selected from the group consisting of Formula 1 or an enantiomeric mixture thereof:
wherein:
the D enantiomer selected from the group consisting of Formula 1a predominates and:
Rx, R1 and R2 are preferably selected from hydrogen,
This is O-carbamoyl-(D)-phenylalaninol, which can also be named (R)-(beta-amino-benzenepropyl) carbamate monohydrochloric acid, Formula 1b below; also referred to herein as "test compound"

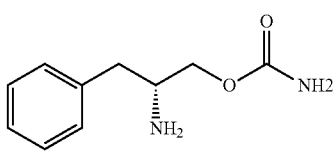

Formula 1b

This is the dextrorotary (D) enantiomer that is of absolute configuration (R).

For enantiomeric mixtures wherein one enantiomer selected from the group consisting of Formula 1 predominates, preferably, an enantiomer selected from the group consisting of Formula 1 predominates to the extent of about 90% or greater.

More preferably, an enantiomer selected from the group consisting of Formula 1 predominates to the extent of about 98% or greater.

The compounds of Formula 1 can be synthesized by methods known to a skilled artisan. Some reaction schemes for synthesizing compounds of Formula (I) have been described in published; U.S. Pat. Nos. 5,705,640, 5,756,817, 5,955,499, and 6,140,532.

Details of the above reactions schemes as well as representative examples on the preparation of specific compounds have been described in published; U.S. Pat. Nos. 5,705,640, 5,756,817, 5,955,499, 6,140,532, all incorporated herein by reference in their entirety.

The salts and esters of the compounds of Formula (I) can be produced by treating the compound with an acid (HX) in suitable solvent or by means well known to those of skill in the art.

From Formula 1 it is evident that some of the compounds of the invention have at least one and possibly more asymmetric carbon atoms. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J.F.W. McOmie, Plenum Press, 1973; and T.W. Greene & P.G.M. Wuts, Protective Groups in Organic Synthesis, Third Edition, John Wiley & Sons, 1999. The protecting groups may be removed at a convenient subsequent stage using methods known from the art.

The present invention is based in part on the discovery that phenylalkylamino carbamates of Formula 1 discussed above have novel and unique pharmacological properties. These compounds have been shown in both an animal model and by signals seen in the side effects reported in clinical studies in humans to have the ability to treat sexual dysfunction in both male and females.

Although the precise mechanism of action is not completely understood it is known that these compounds do not work by the same mechanisms as most other known treatments for sexual dysfunction. For these reasons the compounds of Formula 1 are especially suitable for use as sole or adjunctive treatment for sexual dysfunction or in combination with other medications that are known to produce sexual dysfunction as a side effect so as to minimize or eliminate this side effect.

Thus, these compounds can be safely used alone or in combination with other useful medications to provide enhanced efficacy and reduced side effects because of the smaller doses of each drug that can be used.

In one aspect, this invention relates to methods to treat a female or a male suffering from sexual dysfunction; the method comprising delivering to the subject a therapeutically effective amount of one or more of the carbamate compounds of the invention or a pharmaceutically acceptable salt or ester thereof and a pharmaceutically acceptable carrier, diluent or excipient.

In a further aspect, the present invention relates to methods to eliminate, reduce or counter the sexual dysfunction produced by other medications by means of co administration. Therefore, embodiments of the invention also include methods wherein the carbamate compounds of the invention are administered concomitantly or sequentially with other medications that may themselves cause sexual dysfunction in order to prevent, reverse or minimizes this unwanted side effect.

Therefore in the methods of this invention these carbamate compounds can be added or combined in a regimen with one or more other medications including antidepressants or other medications to produce a combination with decreased sexual dysfunction side effects. This may allow the patient to tolerate higher doses of the required medication and so result in increased therapeutic efficacy and/or improved quality of life for the patient.

Thus, in some embodiments of this invention, the subject or patient is already stabilized on the antidepressant or other medication but may be showing significant sexual dysfunction as a side effect. In this embodiment, the compound of Formula 1 is added to the existing regimen in doses of 1.0 mg to 100.00 mg/day increments until the sexual dysfunction induced by the first medication is reduced or eliminated. One of skill in the art can assess reduction in side effects through clinical interviews or questionnaires that measure symptoms.

In other embodiments, the antidepressant or other medication is started simultaneously with the compound of Formula 1; this is concomitant administration. In this embodiment the intention would be to provide a prophylactically effective amount of a compound of Formula 1 in order to prevent the development of sexual dysfunction due to the conventional antidepressant or other medication. In embodiments in which both medications are started simultaneously the prophylactically effective doses of compounds of Formula. 1 would be determined by side effects and response. Typically, prophylactically effective doses of a compound of Formula 1 would start at 25-50 mg/day and increase in increments of about 25-50 mg./day per week until side effects intervene or an adequate response is obtained. One of skill in the art could readily determine appropriate doses of the antidepressant or other medication from the manufactures recommendations and the response and side effects experienced by the patient.

Compounds of the present invention (compounds of Formula 1) or enantiomers, diastereomers, racemates or mixtures thereof, or hydrates, solvates and pharmaceutically acceptable salts, esters and amides thereof may be used to provide treatment, either prophylactically or after their development, for the serious adverse side effect of sexual dysfunction in both males and females for many medications.

Such medications include but are not limited to; conventional antidepressants and other psychiatric medications that include but are not limited to; selective serotonin reuptake inhibitors (SSRI's); selective serotonin and norepinephrine reuptake inhibitors (SNRI's); older tricyclic antidepressants (TCAs); monoamine oxidase inhibitors (MAO-inhibitors), reversible inhibitors of monoamine oxidase (RIMAs), tertiary amine tricyclics and secondary amine tricyclic antidepressants, antipsychotics, anticonvulsants, lithium carbonate, and including but not limited to fluoxetine, duloxetine, venlafaxine, milnacipran, citalopram, fluvoxamine, paroxetine, sertraline, 5-MCA-NAT, lithium carbonate (liCO$_3$), isocarboxazid, pheneizine, tranylcypromine, selegiline, moclobemide, amitriptyline, clomipramine, doxepin, imipramine, trimipramine, amoxapine, desipramine, maprotiline, nortriptyline and protriptyline, kappa opioid receptor antagonists; selective neurokinin antagonists, corticotropin releasing factor (CRF) antagonists, antagonists of tachykinins, α-adrenoreceptor antagonists, and other types of medications such as; antihypertensive medications, cardiac medications such as calcium channel blockers, ACE inhibitors, statins, etc and pharmaceutically acceptable salts or esters thereof.

The Test Compound

One compound of Formula 1, (referred to herein as "test compound" is (R)-beta-amino-benzenepropyl) carbamate monohydrochloric acid, also called O-carbamoyl-(D)-phenylalaninol

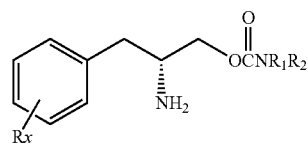

Wherein R, R1 and R2 are hydrogen and x is 1. this is the dextrorotary enantiomer that is of absolute configuration (R).

This compound has been tested in animal models and in humans and has demonstrated effects that strongly support the value of this group of compounds in treating sexual dysfunction, as discussed below.

In humans, the test compound has shown a significant signal in the trial conducted to assess the compounds antidepressant effects. This was a large placebo controlled study where the test compound was compared with a conventional SSRI antidepressant (Paroxetine). An analysis of the post trial questionnaires shows an effect of increasing interest in sex and in ability to have an orgasm mostly in males with the peak effect occurring at a dose of 400 mg per day. This study was not designed to see or evaluate this property of the compound and so future studies directed specifically to assess this property of test compound in humans will be performed.

Test compound has also shown activity in an animal model that would support the use of the compounds of the invention as treatments for sexual dysfunction (See below).

EXAMPLE 1

In rats and mice, the test compound has antidepressant effects and at higher dose stimulant-like effects on locomotor activity. Although the mechanism of action of test compound is unknown, this pharmacological profile may involve activation of central catecholaminergic pathways. In addition to antidepressant effects, increased central catecholaminergic activity is also known to increase sexual behavior in laboratory animals and patients (See, Foreman M M and Hall J L, "Effects of D$_2$-dopaminergic receptor stimulation on the lordotic response of female rats." Psychopharmacology 91:96-100, 1987 and Foreman M M: "Disorders of sexual response: Pioneering new pharmaceutical and therapeutic opportunities." Exp. Opin. Invest. Drugs 4:621-636, 1995.).

For initial preclinical evaluation of the effects on sexual behavior, the following study was conducted to evaluate the effects of test compound on lordotic response in the ovariectomized estrogen treated rat.

Materials and Methods

Animals: Long-Evans hooded female rates (100-125 g) male Sprague-Dawley rats (150-175 g) were obtained from Charles River Breeding laboratories.

Chemicals: Progesterone (Cat. # P-0130; Lot 128H0456) and estrone (Cat # E-9750; Lot 28H0372) were purchased from Sigma Chemical Company and quinelorane Cat # Q-110; Lot PRF-694A) and bupropion (Cat # B-102; BS-11-10) were purchased from Research Biochemicals Incorporated. Test compound (Lot # D5-91B) was synthesized at SK Biopharmaceutical Center, Fairfield, N.J. Estrone and progesterone were dissolved in propylene glycol (Fisher Scientific P355-1; Lot # 992032). test compound, quinelorane and bupropion were dissolved in sterile saline (0.9% NaCl, Abbott Laboratories Lot #25-270-DK).

Protocol for ovariectomy: Female rats (108-120 g) were anesthetized with 100 mg/kg s.c. ketamine (Ketaset 100 mg/ml, Ford Dodge Laboratories, lot #440339) and 7 mg/kg s.c. xylazine (Rompun 20 mg/ml, Bayer Corporation, lot #26050E). A midline incision (1 cm) on the ventral surface was made starting approximately 0.5-1 cm from the genitalia. A second incision (1 cm) was through the linea alba connecting fascia for abdominal muscles. The body of the uterus was located near the pubic bone and retracted through the abdominal incision. The uterine horns with ovaries were retracted through the abdominal wall. Each uterine horn was ligated near the uterine body bisected and removed. The abdominal, wall was closed with 2 sutures and the skin incision was closed with either wound clips or sutures. The rats were kept warm until they recovered from the anesthesia. OVX=ovariectomized.

Accelerated light cycle (10:14): Lights were on from 1 am to 11 am. During dark phase, the room was kept dark except for lighting from red lights needed to observe the behaviors.

Behavior observation arenas: Side walls (45×60 cm) and top (60×60 cm) with hole (15×15 cm) were constructed of clear Lucite plastic and bonded together with adhesive. The base was made from stainless steel grating and was placed over bedding material. Arenas and base were washed between experiments.

Protocol for female sexual behavior: At least 2-3 hours into the dark phase of the lighting cycle, male rats are placed into the behavior arenas and allowed to acclimate for 15 minutes prior to testing. Prior to the testing of experimental animals, the males are exposed to sexually receptive, OVX rats treated with estrone 0.25 mg s.c. 48 hours prior to test and progesterone 1 mg s.c. 6 hours prior to test. When active mating occurs, the receptive females are removed. The test female (OVX treated only with estrone 0.25 mg 48 hours prior to test) is added to the arena with the activated male. The number of lordosis responses for 15 mounts is recorded (lordosis is defined as a downward arching of the back to expose genitalia).

During this first test period, only female rats with a L/M of 4/15 or lower were treated with test drug and 90 minutes later the rats were retested as previously for 15 mounts. This exclusion criterion is used to lower the variance due to rats that become overly receptive to estrone. The index of change is the change in L/M between test 2 and test 1. Statistical comparisons of the treatment groups were made using ANOVA followed by a Dunnett's test for multiple treatment group designs and a Student's t test for single control and treatment designs with the minimum level of significance set at p<0.05.

Results

Test compound produced dose-related increases in lordotic behavior in the female rat at doses of 10, 30 and 100 mg/kg s.c. (Table 1) (See also FIG. 1) test compound at 30 and 100 mg/kg produced significantly greater lordotic response than vehicle treatment. For reference, some of these animals were subsequently treated with either quinelorane (25 μg/kg s.c.) or bupropion (30 mg/kg s.c.). Both quinelorane and bupropion produced significant increases in lordotic response compared to vehicle treatment.

TABLE 1

Effects of test compound (TC) on Lordotic Response

| Treatment | Number of Rats | Change in Lordotic Response |
|---|---|---|
| Vehicle (saline) | 22 | 0.201 +/− 0.042 |
| TC 10 mg/kg s.c. | 23 | 0.338 +/− 0.049 |
| TC 10A 30 mg/kg s.c. | 15 | 0.476 +/− 0.049 * |
| TC 10A 100 mg/kg s.c. | 14 | 0.559 +/− 0.059 * |

* = significantly different from vehicle control by ANOVA, Dunnett's test.

TABLE 2

Effects of Quinelorane on Lordotic Response

| Treatment | Number of Rats | Change in Lordotic Response |
|---|---|---|
| Vehicle (saline) | 9 | 0.174 +/− 0.062 |
| Quinelorane 25 μg/kg s.c. | 9 | 0.593 +/− 0.056 * |

* = significantly different from vehicle control by Student's test.

TABLE 3

Effects of Bupropion on Lordotic Response

| Treatment | Number of Rats | Change in Lordotic Response |
|---|---|---|
| Vehicle (saline) | 9 | 0.174 +/− 0.066 |
| Bupropion 30 mg/kg s.c. | 9 | 0.478 +/− 0.073 * |

* = significantly different from vehicle control by Student's test.

Discussion

One of the potential clinical indications of test compound is for the treatment of depression. (See, Foreman M M: "Disorders of Sexual Response: Pioneering new pharmaceutical and therapeutic opportunities." Exp. Opin. Invest. Drugs 4:621-636, 1995)

Since many antidepressants are known to suppress sexual response, the preceding studies serve as an evaluation of this potential side effect. In the current studies, treatment with test compound produced dose-related increases in lordotic responses to mounting. The magnitude of these effects were similar to quinelorane and bupropion, which are known to augment sexual response in patients. (See, Foreman M M: "Disorders of sexual response: Pioneering new pharmaceutical and therapeutic opportunities." Exp. Opin. Invest. Drugs 4:621-636, 1995)

These studies provide preliminary evidence that test compound will not suppress sexual responses, but may augment sexual response. Since the responses observed are similar to two compounds that augment sexual responses in clinical trials, test compound could be used for the treatment of sexual disorders.

Summary

Test compound produced dose-related increases in lordotic response in the ovariectomized, estrogen treated rat with statistical significance at 30 and 100 mg/kg s.c.

The magnitude of effects (efficacy) of test compound was similar to that observed with quinelorane and bupropion, compounds that reportedly increase sexual response in patients.

These findings provide preliminary evidence that test compound will not suppress sexual response and that test compound could be useful for the treatment of sexual disorders.

Use of Compounds of Invention to Treat Sexual Dysfunction Side Effects of Other Medications As used herein the term "antidepressant" shall mean any compound known to possess antidepressant action in mammals that can be used in combination with the carbamate compounds of the present invention. Many of the most commonly used antidepressants produce the serious, adverse side effect of sexual dysfunction in both males and females. Thus, the term includes but is not limited to: selective serotonin reuptake inhibitors (SSRI's); selective serotonin and norepinephrine reuptake inhibitors (SNRI's); older tricyclic antidepressants; bupropion and MAO inhibitors.

Selective serotonin reuptake inhibitors (SSRI's) and selective serotonin and norepinephrine reuptake inhibitors (SNRI's) include, but are not limited to:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson et al., J. Med. Chem, 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers.

Duloxetine, N-methyl-3-(1-naphthalenyloxy)-3-(2-thienyl) propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule;

Venlafaxine is known in the literature, and U.S. Pat. No. 4,761,501 teaches its method of synthesis and its activity as an inhibitor of serotonin and norepinephrine uptake. Venlafaxine is identified as compound A in that patent;

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret et al., Neuropharmacology 24, 1211-19 (1985), describe its pharmacological activities as an inhibitor of serotonin and norepinephrine reuptake;

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen et al., Eur. J. Pharmacol. 41,153 (1977), and reports of its clinical effectiveness in depression may be found in Dufour et al., Int. Clin. Psychopharmacol. 2, 225 (1987), and Timmerman et al., ibid., 239;

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen et al., Brit. J. Pharmacol. 60, 505 (1977); and De Wilde et al., J. Affective Disord. 4, 249 (1982); and Benfield et al., Drugs 32, 313 (1986);

Paroxetine, trans-(−)-3-[(1,3-benzodioxol-5-yloxy)methyl]-4-(4-fluorophenyl)piperidine, may be found in U.S. Pat. Nos. 3,912,743 and 4,007,196. Reports of the drug's activity are in Lassen, Eur. J. Pharmacol. 47, 351 (1978); Hassan et al., Brit J. Clin. Pharmacol. 19, 705 (1985); Laursen et al., Acta Psychiat. Scand. 71, 249 (1985); and Battegay et al., Neuropsychobiology 13, 31 (1985); and Sertraline, (1S-cis)-4-(3,4-dichlorophenyl)-1,2,3,4-tetrahydro-N-methyl-1-naphthylamine hydrochloride, is a serotonin reuptake inhibitor that is marketed as an antidepressant. It is disclosed by U.S. Pat. No. 4,536,518.

Carbamate compounds of the present invention may also be used in combination with other classes of antidepressants and other therapeutically effective agents including but not limited to, for example; 5-MCA-NAT (e.g., U.S. Pat. No. 6,562,858); lithium carbonate ($liCO_3$), monoamine oxidase inhibitors (MAO-inhibitors), suitable monoamine oxidase inhibitors include: isocarboxazid, pheneizine, tranylcypromine and selegiline, and pharmaceutically acceptable salts thereof; reversible inhibitors of morioamine oxidase (RIMAs), suitable reversible inhibitors of monoamine oxidase include: moclobemide, and pharmaceutically acceptable salts thereof; antiepileptic drugs (AEDs) including but not limited to kappa opioid receptor antagonists (e.g., U.S. Pat. No. 6,528,518); selective neurokinin antagonists (e.g., U.S. Pat. No. 6,436,928) corticotropin releasing factor (CRF) antagonists, suitable CRF antagonists include those compounds described in International Patent Specification Nos. WO 94/13643, WO 94/13644, WO 94/13661, WO 94/13676 and WO 94/13677.; antagonists of tachykinins (e.g., U.S. Pat. No. 6,518,273) and α-adrenoreceptor antagonists.

In addition, the compounds of the present invention can be used to reverse or reduce the sexual dysfunction caused by older antidepressants that are primarily norepinephrine reuptake inhibitors. Such drugs include norepinephrine reuptake inhibitors, include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof.

Suitable examples of secondary amine tricyclics include: amoxapine, desipramine, maprotiline, nortriptyline and protriptyline, and pharmaceutically acceptable salts thereof.

Suitable serotonin and noradrenaline reuptake inhibitors of use in the present invention include: venlafaxine, and pharmaceutically acceptable salts thereof.

Combined use of one or more of the compounds of the invention with any of the above described antidepressants may reduce, lessen or eliminate the serious, adverse side effect of sexual dysfunction produced by these drugs in both males and females.

All of the U.S. patents that have been mentioned above in connection with compounds used in the present invention are incorporated herein by reference.

Definitions

For convenience, certain terms employed in the specification, examples, and appended claims are collected here.

It is to be understood that this invention is not limited to the particular methodology, protocols, animal species or genera, and reagents described, as such may vary. It is also to be understood that the terminology used herein is for the purpose of describing particular embodiments only, and is not intended to limit the scope of the present invention that will be limited only by the appended claims.

As used herein the term "subject", refers to an animal, preferably a mammal, and most preferably a human both male and female, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the signs or symptoms of the disease or disorder being treated.

The term "prophylactically effective amount" is intended to mean that amount of a pharmaceutical drug that will prevent or reduce the risk of occurrence of the biological or medical event that is sought to be prevented of a tissue, a system, animal or human that is being sought by a researcher, veterinarian, medical doctor or other clinician.

The term "pharmaceutically acceptable salts or esters" shall mean non-toxic salts or esters of the compounds employed in this invention which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Therefore, the term "a patient in need of treatment" as used herein will refer to any subject or patient who currently has or may develop any of the above syndromes or disorders, including any mood disorder which can be treated by antidepressant medication, or any other disorder in which the patient's present clinical condition or prognosis could benefit from the administration of one or more compounds of Formula (I) alone or in combination with another therapeutic intervention including but not limited to another medication.

The term "treating" or "treatment" as used herein, refers to any indicia of success in the prevention or amelioration of an injury, pathology or condition such as sexual dysfunction, including any objective or subjective parameter such as abatement; remission; diminishing of symptoms or making the injury, pathology, or condition more tolerable to the patient; slowing in the rate of degeneration or decline or worsening of the illness; making the final point of worsening less debilitating; or improving a subject's physical or mental well-being. The treatment or amelioration of symptoms can be based on objective or subjective parameters; including the results of a physical examination, neurological examination, and/or psychiatric evaluations. Accordingly, the term "treating" or "treatment" includes the administration of the compounds or agents of the present invention for treatment of any form of sexual dysfunction in both males and females. In some instances, treatment with the compounds of the present invention will done in combination with other compounds to prevent, inhibit, or arrest the progression of the mood disorder.

The term 'therapeutic effect' as used herein, refers to the effective improvement in or reduction of symptoms of sexual dysfunction.

The term "a therapeutically effective amount" as used herein means a sufficient amount of one or more of the compounds of the invention to produce a therapeutic effect, as defined above, in a subject or patient in need of such neuroprotection treatment.

The terms "subject" or "patient" are used herein interchangeably and as used herein mean any mammal including but not limited to human beings including a human patient or subject to which the compositions of the invention can be administered. The term mammals include human patients, both male and female and non-human primates, as well as experimental animals such as rabbits, rats, and mice, and other animals.

Methods are known in the art for determining therapeutically and prophylactically effective doses for the instant pharmaceutical composition. For example the compound can be employed at a daily dose in the range of about 0.1 mg to 400 mg usually on a regimen of 1 to 2 times per day, for an average adult human. The effective amount, however, may be varied depending upon the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compound may be administered to a subject by any conventional route of administration, including, but not limited to, intravenous, oral, subcutaneous, intramuscular, intradermal and parenteral. Depending on the route of administration, compounds of Formula (I) can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

To prepare the pharmaceutical compositions of this invention, one or more compounds of formula (1) or salt thereof as the active ingredient is intimately admixed with a pharmaceutical carrier according to conventional pharmaceutical compounding techniques. Carriers are necessary and inert pharmaceutical excipients, including, but not limited to, binders, suspending agents, lubricants, flavorings, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidyicholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Preferably these compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation.

Alternatively, the composition may be presented in a form suitable for once-weekly or once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 25 to about 400 mg of the active ingredient. Preferably, the range is from about 50 to about 200 mg of the active ingredient.

In some embodiments of the present invention carbamate compounds suitable for use in the practice of this invention will be administered either singly or concomitantly with at least one or more other compounds or therapeutic agents. In these embodiments, the present invention provides methods to treat or prevent sexual dysfunction in a patient. The method includes the step of; administering to a patient in need of treatment, an effective amount of one of the carbamate compounds disclosed herein in combination with an effective amount of one or more other compounds or therapeutic agents that may either cause or them selves have the ability to treat sexual dysfunction or the ability to augment the sexual dysfunction treatment effects of the compounds of the invention.

As used herein the term "concomitant administration" or "combination administration" of a compound, therapeutic agent or known drug with a compound of the present invention means administration of the one or more compounds of the invention at such time that the other therapeutic agent, that may cause sexual dysfunction, is being administered so that the combination will have reduced tendency to cause sexual dysfunction. Such concomitant administration can involve concurrent (i.e. at the same time), prior, or subsequent administration of the other therapeutic agent with respect to the administration of a compound of the present invention. A person of ordinary skill in the art, would have no difficulty determining the appropriate timing, sequence and dosages of administration for particular drugs and compounds of the present invention.

In addition, in some embodiments, the compounds of this invention will be used, either alone or in combination with each other or in combination with one or more other therapeutic medications as described above, or their salts or esters, for manufacturing a medicament for the purpose of providing treatment of sexual dysfunction to a patient or subject in need thereof.

"$C_1$-$C_4$ alkyl" as used herein refers to substituted or unsubstituted aliphatic hydrocarbons having from 1 to 4 carbon atoms. Specifically included within the definition of "alkyl" are those aliphatic hydrocarbons that are optionally substituted. In a preferred embodiment of the present invention, the $C_1$-$C_4$ alkyl is either unsubstituted or substituted with phenyl.

The term "phenyl", as used herein, whether used alone or as part of another group, is defined as a substituted or unsubstituted aromatic hydrocarbon ring group having 6 carbon atoms. Specifically included within the definition of "phenyl" are those phenyl groups that are optionally substituted. For example, in a preferred embodiment of the present invention, the, "phenyl" group is either unsubstituted or substituted with halogen, $C_1$-$C_4$ alkyl, $C_1$-$C_4$ alkoxy, amino, nitro, or cyano.

It is understood that substituents and substitution patterns on the compounds of the present invention can be selected by one of ordinary skill in the art to provide compounds that are chemically stable and that can be readily synthesized by techniques known in the art as well as the methods provided herein.

Representative 2-phenyl-1,2-ethanediol monocarbomates and dicarbamates include, for example, the following compounds:

The present invention includes the use of isolated enantiomers of Formula 1. In one preferred embodiment, a pharmaceutical composition comprising the isolated S-enantiomer of Formula 1 is used to provide adjuvant antidepressant efficacy in a subject. In another preferred embodiment, a pharmaceutical composition comprising the isolated R-enantiomer of Formula 1 is used to provide adjuvant antidepressant efficacy a subject The present invention also includes the use of mixtures of enantiomers of Formula 1. In one aspect of the present invention, one enantiomer will predominate. An enantiomer that predominates in the mixture is one that is present in the mixture in an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one preferred embodiment, the enantiomer that predominates in a composition comprising a compound of Formula 1 is the S-enantiomer of Formula 1.

The present invention provides methods of using enantiomers and enantiomeric mixtures of compounds represented by Formula 1. A carbamate enantiomer of Formula 1 contains an asymmetric chiral carbon at the benzylic position, which is the second aliphatic carbon adjacent to the phenyl ring.

An enantiomer that is isolated is one that is substantially free of the corresponding enantiomer. Thus, an isolated enantiomer refers to a compound that is separated via separation techniques or prepared free of the corresponding enantiomer. The term "substantially free," as used herein, means that the compound is made up of a significantly greater proportion of one enantiomer. In preferred embodiments, the compound includes at least about 90% by weight of a preferred enantiomer. In other embodiments of the invention, the compound includes at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein.

Carbamate Compounds as Pharmaceuticals:

The present invention provides racemic mixtures, enantiomeric mixtures and isolated enantiomers of Formula 1 as pharmaceuticals. The carbamate compounds are formulated as pharmaceuticals to provide adjuvant antidepressant action in a subject.

In general, the carbamate compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intacerebroventricular, intrathecal, intracisternal, intraspinal or peri-spinal routes of administration by delivery via intracranial or intravertebral needles or catheters with or without pump devices.

Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: *Remington's Pharmaceutical Sciences,* 17th ed., Mack Publishing Company, Easton Pa., 1985, the disclosure of which is incorporated herein by reference in its entirety and for all purposes. Suitable liquid carriers, especially for injectable solutions, include water, aqueous saline solution, aqueous dextrose solution, and glycols.

The carbamate compounds can be provided as aqueous suspensions. Aqueous suspensions of the invention can contain a carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol monooleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these.

Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally acceptable diluents or solvent, such as a solution of 1,3-butanediol. The formulations of commends can be presented in unit-dose or multi-dose sealed containers, such as ampoules and vials. Injection solutions and suspensions can be prepared from sterile powders, granules, and tablets of the kind previously described.

A carbamate compound suitable for use in the practice of this invention can be and is preferably administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 50% w of the carbamate compound, preferably 0.00001% w to 25% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient.

Formulations suitable for oral administration can consist of (a) liquid solutions, such as an effective amount of the pharmaceutical formulation suspended in a diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropyl-methyl-cellulose or sodium carboxymethylcellulose; and gums including arabic and tragacanth; as well as proteins such as gelatin and collagen.

If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention.

In another embodiment, the compounds of the present invention can be delivered by the use of liposomes which fuse with the cellular membrane or are endocytosed, i.e., by employing ligands attached to the liposome that bind to surface membrane protein receptors of the cell resulting in endocytosis. By using liposomes, particularly where the liposome surface carries ligands specific for target cells, or are otherwise preferentially directed to a specific organ, one can focus the delivery of the carbamate compound into target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation can be a lyophilized powder which can contain, for example, any or all of the following: 1 mM-50 mM histidine, 0.1%-2% sucrose, 2%-7% mannitol, at a pH range of 4.5 to 5.5, that is combined with buffer prior to use.

Pharmaceutically acceptable salts and esters refer to salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like. Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds. When there are two acidic groups present, a pharmaceutically acceptable salt or ester may be a mono-acid-mono-salt or ester or a di-salt or ester; and similarly where there are more than two acidic groups present, some or all of such groups can be salified or esterified.

Compounds named in this invention can be present in unsalified or unesterified form, or in salified and/or esterified form, and the naming of such compounds is intended to include both the original (unsalified and unesterified) compound and its pharmaceutically acceptable salts and esters. The present invention includes pharmaceutically acceptable salt and ester forms of Formula (1). More than one crystal form of an enantiomer of Formula 1 can exist and as such are also included in the present invention.

A pharmaceutical composition of the invention can optionally contain, in addition to a carbamate compound, at least one other therapeutic agent useful in the treatment of sexual dysfunction. For example the carbamate compounds of Formula 1 can be combined physically with other sexual dysfunction treatments in fixed dose combinations to simplify their administration.

Methods of formulating pharmaceutical compositions have been described in numerous publications such as *Pharmaceutical Dosage Forms: Tablets*. Second Edition. Revised and Expanded. Volumes 1-3, edited by Lieberman et al; *Pharmaceutical Dosage Forms*: Parenteral Medications. Volumes 1-2, edited by Avis et al; and *Pharmaceutical Dosage Forms: Disperse Systems*. Volumes 1-2, edited by Lieberman et al; published by Marcel Dekker, Inc, the disclosure of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

Dosage Regimens

The present invention provides methods of providing adjuvant antidepressant action in a mammal using carbamate compounds. The amount of the carbamate compound necessary to reduce or prevent sexual dysfunction is defined as a therapeutically or a pharmaceutically effective dose. The dosage schedule and amounts effective for this use, i.e., the dosing or dosage regimen will depend on a variety of factors including the stage of the disease, the patient's physical status, age and the like. In calculating the dosage regimen for a patient, the mode of administration is also taken into account.

A person of ordinary skill in the art will be able without undue experimentation, having regard to that skill and this disclosure, to determine a therapeutically effective amount of a particular substituted carbamate compound for practice of this invention (see, e.g., Lieberman, Pharmaceutical Dosage Forms (Vols. 1-3, 1992); Lloyd, 1999. The art, Science and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times daily, 3 times per week, or weekly. In one embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to provide antidepressant action. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

The active compound present in these unit dosage forms of the composition can be present in an amount of, for example, from about 10 mg. to about one gram or more, for single or multiple daily administration, according to the particular need of the patient. By initiating the treatment regimen with a minimal daily dose of about one gram, the blood levels of the carbamate compounds can be used to determine whether a larger or smaller dose is indicated.

Effective administration of the carbamate compounds of this invention can be administered, for example, at an oral or parenteral dose of from about 0.01 mg/kg/dose to about 150 mg/kg/dose. Preferably, administration will be from about 0.1/mg/kg/dose to about 25 mg/kg/dose, more preferably from about 0.2 to about 18 mg/kg/dose. Therefore, the therapeutically effective amount of the active ingredient contained per dosage unit as described herein can be, for example, from about 1 mg/day to about 7000 mg/day for a subject having, for example, an average weight of 70 kg.

The methods of this invention also provide for kits for use in providing treatment of sexual dysfunction. After a pharmaceutical composition comprising one or more carbamate compounds of this invention, with the possible addition of one or more other compounds of therapeutic benefit, has been formulated in a suitable carrier, it can be placed in an appropriate container and labeled for providing adjuvant antidepressant action. Additionally, another pharmaceutical comprising at least one other therapeutic agent useful in the provide antidepressant action can be placed in the container as well and labeled for treatment of the indicated disease.

Such labeling can include, for example, instructions concerning the amount, frequency and method of administration of each pharmaceutical.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation. The following examples are provided to illustrate specific aspects of the invention and are not meant to be limitations.

References Cited

All references cited herein are incorporated herein by reference in their entirety and for all purposes to the same extent as if each individual publication or patent or patent application was specifically and individually indicated to be incorporated by reference in its entirety for all purposes.

The discussion of references herein is intended merely to summarize the assertions made by their authors and no admission is made that any reference constitutes prior art. Applicants reserve the right to challenge the accuracy and pertinence of the cited references.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein will be apparent to those skilled in the art from the foregoing description and accompanying drawings. Such modifications and variations are intended to fall within the scope of the appended claims. The present invention is to be limited only by the terms of the appended claims, along with the full scope of equivalents to which such claims are entitled.

What is claimed is:

1. A method of treating sexual dysfunction, in a subject by increasing interest in sex and the ability to have an orgasm, comprising the step of the administration, to a subject in need of such treatment, of a therapeutically effective amount of a compound of the Formula (1):

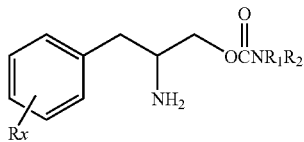

(I)

or a pharmaceutically acceptable salt or ester thereof:
wherein R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; or $R_1$ and $R_2$ can be joined to form a 5 to 7-membered heterocycle substituted with a member selected from the group consisting of hydrogen, alkyl, and aryl groups, wherein the heterocycle can comprise 1 to 2 nitrogen atoms and 0 to 1 oxygen atom, wherein the nitrogen atoms are not directly connected with each other or with the oxygen atom.

2. The method of claim 1 wherein R, $R_1$ and $R_2$ are hydrogen and x=1.

3. The method of claim 1 wherein the compound of Formula 1 is an enantiomer substantially free of other enantiomers or an enantiomeric mixture wherein one enantiomer of Formula 1 predominates;

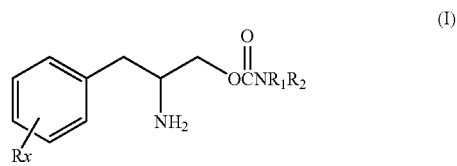

(I)

or a pharmaceutically acceptable salt or ester thereof;
wherein;

R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; or $R_1$ and $R_2$ can be joined to form a 5 to 7-membered heterocycle substituted with a member selected from the group consisting of hydrogen, alkyl, and aryl groups, wherein the heterocycle can comprise 1 to 2 nitrogen atoms and 0 to 1 oxygen atom, wherein the nitrogen atoms are not directly connected with each other or with the oxygen atom.

4. The method of claim 3 wherein the enantiomer selected from the group consisting of Formula 1 is an enantiomer selected from the group consisting of Formula 1a

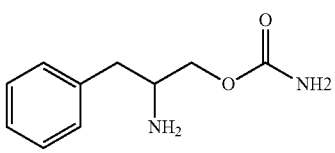

Formula 1a or a pharmaceutically acceptable salt or ester thereof.

5. The method of claim 4 wherein one enantiomer selected from the group consisting of Formula 1a predominates to the extent of about 98% or greater.

6. The method of claim 3 wherein the enantiomer of Formula 1 substantially free of other enantiomers is the dextrorotary (D) enantiomer that is of absolute configuration (R) of Formula 1b or an enantiomeric mixture wherein the enantiomer of Formula 1b, O-carbamoyl-(D)-phenylalaminol, that can also be named (R)-(beta-amino-benzenepropyl) carbamate monohydrochloric acid, predominates

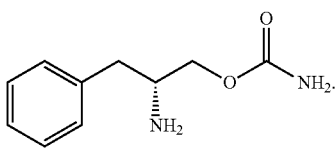

Formula 1b

7. The method of claim 6 wherein the enantiomer of Formula 1b predominates to the extent of about 98% or greater.

8. The method of claim 6 wherein the therapeutically effective amount of enantiomer is from about 0.01 mg/kg/dose to about 300 mg/kg/dose.

9. A method of treating a subject in need of treatment with a therapeutic agent by the administration of said therapeutic agent, wherein said therapeutic agent may cause sexual dysfunction, the method further comprising treating the sexual dysfunction of the subject by increasing interest in sex and the ability to have an orgasm by the concomitant administration to the subject of a therapeutically effective amount of an enantiomer of Formula 1 substantially free of other enantiomers or an enantiomeric mixture wherein one enantiomer of Formula 1 predominates;

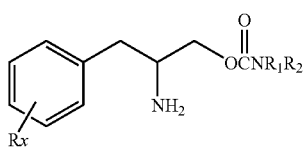

(I)

or a pharmaceutically acceptable salt or ester thereof; wherein;

R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; or $R_1$ and $R_2$ can be joined to form a 5 to 7-membered heterocycle substituted with a member selected from the group consisting of hydrogen, alkyl, and aryl groups, wherein the heterocycle can comprise 1 to 2 nitrogen atoms and 0 to 1 oxygen atom, wherein the nitrogen atoms are not directly connected with each other or with the oxygen atom.

10. The method of claim 9, wherein the enantiomer selected from the group consisting of Formula 1 is an enantiomer selected from the group consisting of Formula 1a

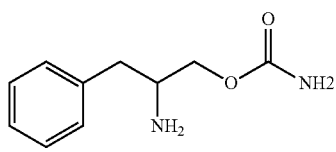

Formula 1a or a pharmaceutically acceptable salt or ester thereof.

11. The method of claim 10 wherein one enantiomer selected from the group consisting of Formula 1a predominates to the extent of about 98% or greater.

12. The method of claim 9, wherein the enantiomer of Formula 1 substantially free of other enantiomers is the dextrorotary (D) enantiomer that is of absolute configuration (R) of Formula 1b or an enantiomeric mixture wherein the enantiomer of Formula 1b, O-carbamoyl-(D)-phenylalaminol, that can also be named (R)-(beta-amino-benzenepropyl) carbamate monohydrochloric acid

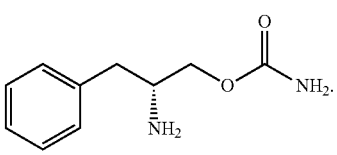

Formula 1b

13. The method of claim 12 wherein the enantiomer of Formula 1b predominates to the extent of about 98% or greater.

14. The method of claim 12 wherein the therapeutic agent is chosen from the group consisting of; selective serotonin reuptake inhibitors (SSRI's); selective serotonin and norepinephrine reuptake inhibitors (SNRI's); older tricyclic antidepressants (TCAs); monoamine oxidase inhibitors (MAO-inhibitors), reversible inhibitors of monoamine oxidase (RIMAs), tertiary amine tricyclics and secondary amine tricyclic antidepressants.

15. The method of claim 12 wherein the therapeutic agent is chosen from the group consisting of; fluoxetine, duloxetine, venlafaxine, milnacipran, citalopram, fluvoxamine, paroxetine, sertraline, 5-MCA-NAT, lithium carbonate (liCO.sub.3), isocarboxazid, phenelzine, tranylcypromine, selegiline, moclobemide, kappa opioid receptor antagonists; selective neurokinin antagonists, corticotropin releasing factor (CRF) antagonists, antagonists of tachykinins, .alpha.-adrenoreceptor antagonists, amitriptyline, clomipramine, doxepin, imipramine, venlafaxine, trimipramine, amoxapine, desipramine, maprotiline, nortriptyline and protriptyline, and pharmaceutically acceptable salts thereof.

16. The method of claim 12 wherein the therapeutically effective amount of enantiomer is from about 0.01 mg/kg/dose to about 300 mg/kg/dose.

17. A method of treating female sexual dysfunction in a subject comprising the step of the administration, to a subject in need of such treatment, of a therapeutically effective amount of a compound of the Formula (1):

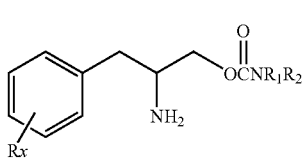

(I)

or a pharmaceutically acceptable salt or ester thereof:

wherein

R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

R₁ and R₂ can be the same or different from each other and are independently selected from the group consisting of hydrogen, lower alkyl of 1 to 8 carbon atoms, aryl, arylalkyl, cycloalkyl of 3 to 7 carbon atoms; or R₁ and R₂ can be joined to form a 5 to 7-membered heterocycle substituted with a member selected from the group consisting of hydrogen, alkyl, and aryl groups, wherein the heterocycle can comprise 1 to 2 nitrogen atoms and 0 to 1 oxygen atom, wherein the nitrogen atoms are not directly connected with each other or with the oxygen atom.

18. The method of claim 17 wherein R, R₁ and R₂ are hydrogen and x=1.

19. The method of claim 17, wherein the compound of Formula 1 is an enantiomer of Formula 1 substantially free of other enantiomers or an enantiomeric mixture wherein one enantiomer of Formula 1 predominates;

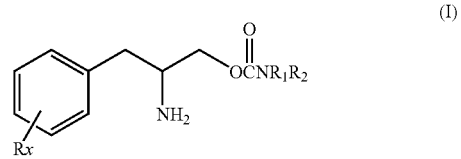

(I)

or a pharmaceutically acceptable salt or ester thereof; wherein;

R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

R₁ and R₂ can be the same or different from each other and are independently selected from the group consisting of hydrogen, lower alkyl of 1 to 8 carbon atoms, aryl, arylalkyl, cycloalkyl of 3 to 7 carbon atoms; or R₁ and R₂ can be joined to form a 5 to 7-membered heterocycle substituted with a member selected from the group consisting of hydrogen, alkyl, and aryl groups, wherein the heterocycle can comprise 1 to 2 nitrogen atoms and 0 to 1 oxygen atom, wherein the nitrogen atoms are not directly connected with each other or with the oxygen atom.

20. The method of claim 19 wherein the enantiomer selected from the group consisting of Formula 1 is an enantiomer selected from the group consisting of Formula 1a

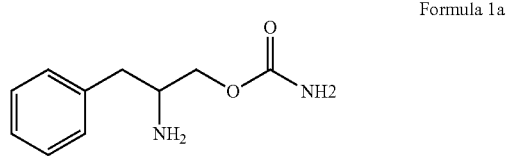

Formula 1a or a pharmaceutically acceptable salt or ester thereof.

21. The method of claim 19 wherein the enantiomer of Formula 1 substantially free of other enantiomers is the dextrorotary (D) enantiomer that is of absolute configuration (R) of Formula 1b or an enantiomeric mixture wherein the enantiomer of Formula 1b, O-carbamoyl-(D)-phenylalaminol, that can also be named (R)-(beta-amino-benzenepropyl) carbamate monohydrochloric acid, predominates

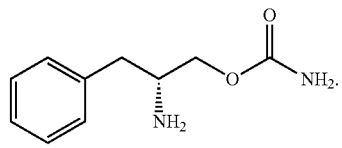

Formula 1b

22. A method of treating sexual dysfunction in a subject by augmenting sexual response comprising the step of the administration, to a subject in need of such treatment, of a therapeutically effective amount of a compound of the Formula (1):

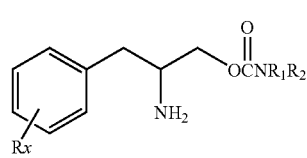

(I)

or a pharmaceutically acceptable salt or ester thereof:

wherein R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

R₁, and R₂ can be the same or different from each other and are independently selected from the group consisting of hydrogen, lower alkyl of 1 to 8 carbon atoms, aryl, arylalkyl, cycloalkyl of 3 to 7 carbon atoms; or R₁ and R₂ can be joined to form a 5 to 7-membered heterocycle substituted with a member selected from the group consisting of hydrogen, alkyl, and aryl groups, wherein the heterocycle can comprise 1 to 2 nitrogen atoms and 0 to 1 oxygen atom, wherein the nitrogen atoms are not directly connected with each other or with the oxygen atom.

23. The method of claim 22 wherein R, R₁ and R₂ are hydrogen and x=1.

24. The method of claim 22, wherein the compound of Formula 1 is an enantiomer of Formula 1 substantially free of other enantiomers or an enantiomeric mixture wherein one enantiomer of Formula 1 predominates;

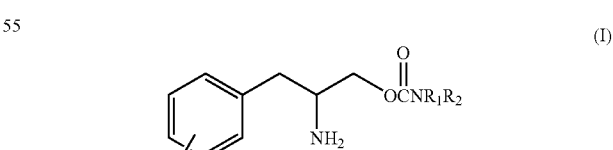

(I)

or a pharmaceutically acceptable salt or ester thereof; wherein;

R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; or $R_1$ and $R_2$ can be joined to form a 5 to 7-membered heterocycle substituted with a member selected from the group consisting of hydrogen, alkyl, and aryl groups, wherein the heterocycle can comprise 1 to 2 nitrogen atoms and 0 to 1 oxygen atom, wherein the nitrogen atoms are not directly connected with each other or with the oxygen atom.

25. The method of claim 24 wherein the enantiomer selected from the group consisting of Formula 1 is an enantiomer selected from the group consisting of Formula 1a

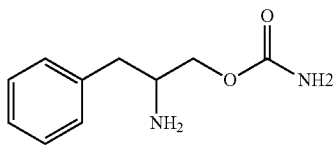

Formula 1a or a pharmaceutically acceptable salt or ester thereof.

26. The method of claim 24 wherein the enantiomer of Formula 1 substantially free of other enantiomers is the dextrorotary (D) enantiomer that is of absolute configuration (R) of Formula 1b or an enantiomeric mixture wherein the enantiomer of Formula 1b, O-carbamoyl-(D)-phenylalaminol, that can also be named (R)-(beta-amino-benzenepropyl) carbamate monohydrochloric acid, predominates

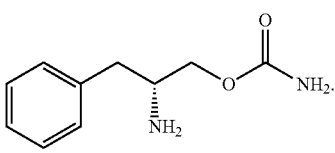

Formula 1b

27. A method of treating a female subject in need of treatment with a therapeutic agent by the administration of said therapeutic agent, wherein said therapeutic agent may cause sexual dysfunction, the method further comprising treating the sexual dysfunction of the subject by the concomitant administration to the subject of a therapeutically effective amount of an enantiomer of Formula 1 substantially free of other enantiomers or an enantiomeric mixture wherein one enantiomer of Formula 1 predominates;

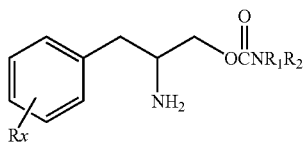

(I)

or a pharmaceutically acceptable salt or ester thereof; wherein;

R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; or $R_1$ and $R_2$ can be joined to form a 5 to 7-membered heterocycle substituted with a member selected from the group consisting of hydrogen, alkyl, and aryl groups, wherein the heterocycle can comprise 1 to 2 nitrogen atoms and 0 to 1 oxygen atom, wherein the nitrogen atoms are not directly connected with each other or with the oxygen atom.

28. The method of claim 27 wherein the enantiomer selected from the group consisting of Formula 1 is an enantiomer selected from the group consisting of Formula 1a

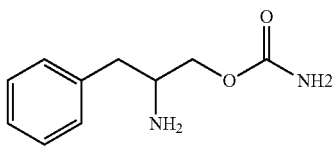

Formula 1a or a pharmaceutically acceptable salt or ester thereof.

29. The method of claim 27 wherein the enantiomer of Formula 1 substantially free of other enantiomers is the dextrorotary (D) enantiomer that is of absolute configuration (R) of Formula 1b or an enantiomeric mixture wherein the enantiomer of Formula 1b, O-carbamoyl-(D)-phenylalaminol, that can also be named (R)-(beta-amino-benzenepropyl) carbamate monohydrochloric acid, predominates

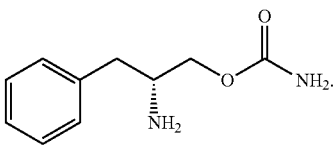

Formula 1b

30. A method of treating a subject in need of treatment with a therapeutic agent by the administration of said therapeutic agent, wherein said therapeutic agent may cause sexual dysfunction, the method further comprising treating the sexual dysfunction of the subject by augmenting the sexual response of the subject by the concomitant administration to the subject of a therapeutically effective amount of an enantiomer of Formula 1 substantially free of other enantiomers or an enan tiomeric mixture wherein one enantiomer of Formula 1 predominates;

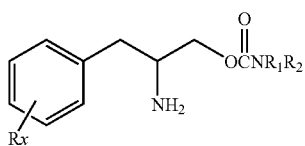
(I)

or a pharmaceutically acceptable salt or ester thereof; wherein;

R is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; or $R_1$ and $R_2$ can be joined to form a 5 to 7-membered heterocycle substituted with a member selected from the group consisting of hydrogen, alkyl, and aryl groups, wherein the heterocycle can comprise 1 to 2 nitrogen atoms and 0 to 1 oxygen atom, wherein the nitrogen atoms are not directly connected with each other or with the oxygen atom.

31. The method of claim 30 wherein the enantiomer selected from the group consisting of Formula 1 is an enantiomer selected from the group consisting of Formula 1a

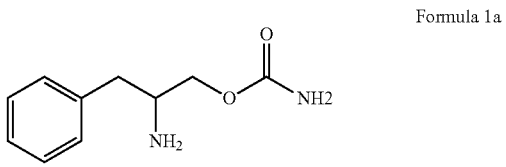 [SMILES: NC(=O)OCC(N)Cc1ccccc1]
Formula 1a or a pharmaceutically acceptable salt or ester thereof.

32. The method of claim 30 wherein the enantiomer of Formula 1 substantially free of other enantiomers is the dextrorotary (D) enantiomer that is of absolute configuration (R) of Formula 1b or an enantiomeric mixture wherein the enantiomer of Formula 1b, O-carbamoyl-(D)-phenylalaminol, that can also be named (R)-(beta-amino-benzenepropyl) carbamate monohydrochloric acid, predominates

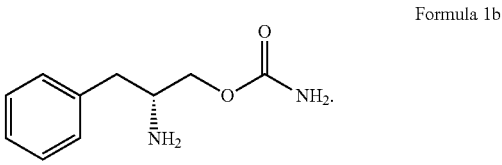 [SMILES: NC(=O)OCC(N)Cc1ccccc1]
Formula 1b

* * * * *

UNITED STATES PATENT AND TRADEMARK OFFICE
CERTIFICATE OF CORRECTION

| | | |
|---|---|---|
| PATENT NO. | : 8,552,060 B2 | Page 1 of 1 |
| APPLICATION NO. | : 11/922128 | |
| DATED | : October 8, 2013 | |
| INVENTOR(S) | : Joseph Palumbo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1386 days.

Signed and Sealed this
Third Day of February, 2015

Michelle K. Lee
*Deputy Director of the United States Patent and Trademark Office*